US012678098B2

(12) United States Patent
Realubit et al.

(10) Patent No.: US 12,678,098 B2
(45) Date of Patent: Jul. 14, 2026

(54) FINGER WEARABLE HEALTH MONITORING DEVICE

(71) Applicant: MOVANO INC., Pleasanton, CA (US)

(72) Inventors: Hector Realubit, North Hollywood, CA (US); Gabriel Cohn, Mill Valley, CA (US); Michael A. Leabman, Pleasanton, CA (US)

(73) Assignee: Movano Inc., Pleasanton, CA (US)

( * ) Notice: Subject to any disclaimer, the term of this patent is extended or adjusted under 35 U.S.C. 154(b) by 225 days.

(21) Appl. No.: 18/345,967

(22) Filed: Jun. 30, 2023

(65) Prior Publication Data

US 2024/0000387 A1 Jan. 4, 2024

Related U.S. Application Data

(60) Provisional application No. 63/358,064, filed on Jul. 1, 2022.

(51) Int. Cl.
*A61B 5/00* (2006.01)
*A61B 5/0205* (2006.01)
*A61B 5/024* (2006.01)

(52) U.S. Cl.
CPC .................................. *A61B 5/6826* (2013.01)

(58) Field of Classification Search
CPC . A61B 5/02438; A61B 5/0002; A61B 5/0205; A61B 5/681; A61B 5/6826
See application file for complete search history.

(56) References Cited

U.S. PATENT DOCUMENTS

| | | |
|---|---|---|
| 10,918,289 B1 | 2/2021 | Wasson et al. |
| 2011/0007035 A1 | 1/2011 | Shai |
| 2015/0182164 A1 | 7/2015 | Utter, II |
| 2015/0220109 A1 | 8/2015 | von Badinski et al. |
| 2021/0173451 A1 | 6/2021 | Daube et al. |
| 2021/0265054 A1 | 8/2021 | Kosman et al. |
| 2021/0289897 A1 | 9/2021 | Hsu et al. |
| 2023/0270384 A1* | 8/2023 | Apoorv ................ A61B 5/6826 |
| | | 600/301 |

FOREIGN PATENT DOCUMENTS

| | | |
|---|---|---|
| IN | 202241010714 B | 2/2022 |
| IN | 202241011816 A | 3/2022 |

* cited by examiner

*Primary Examiner* — Brian T Gedeon
(74) *Attorney, Agent, or Firm* — LOZA & LOZA, LLP

(57) ABSTRACT

A finger wearable health monitoring device is disclosed. In an embodiment, a finger wearable health monitoring device includes a circular metal shell, the circular metal shell comprising a strip of metal that includes an outer surface and an inner surface and two opposing ends, sensor electronics adjacent the inner surface of the circular metal shell, and encapsulant formed over the sensor electronics and on the inner surface of the circular metal shell, and the sensor electronics includes a flexible portion of a circuit board that is opposite the two opposing ends of the circular metal shell.

15 Claims, 19 Drawing Sheets

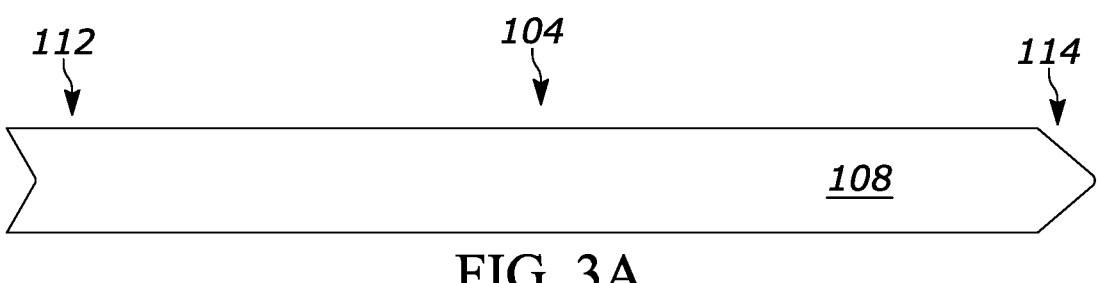
FIG. 3A
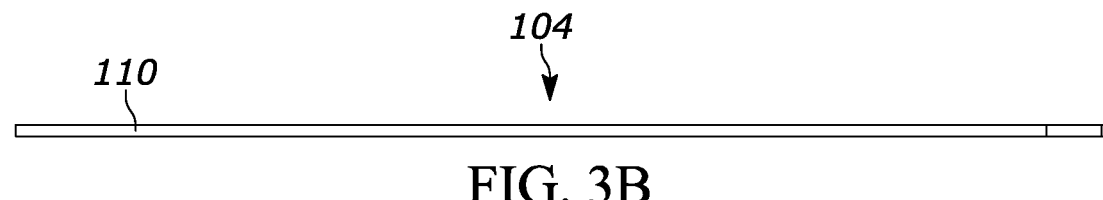
FIG. 3B
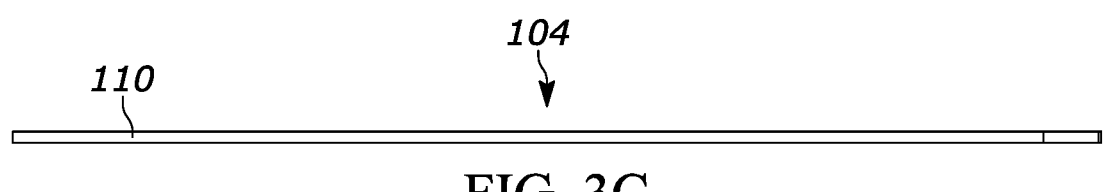
FIG. 3C
FIG. 3D                    FIG. 3E

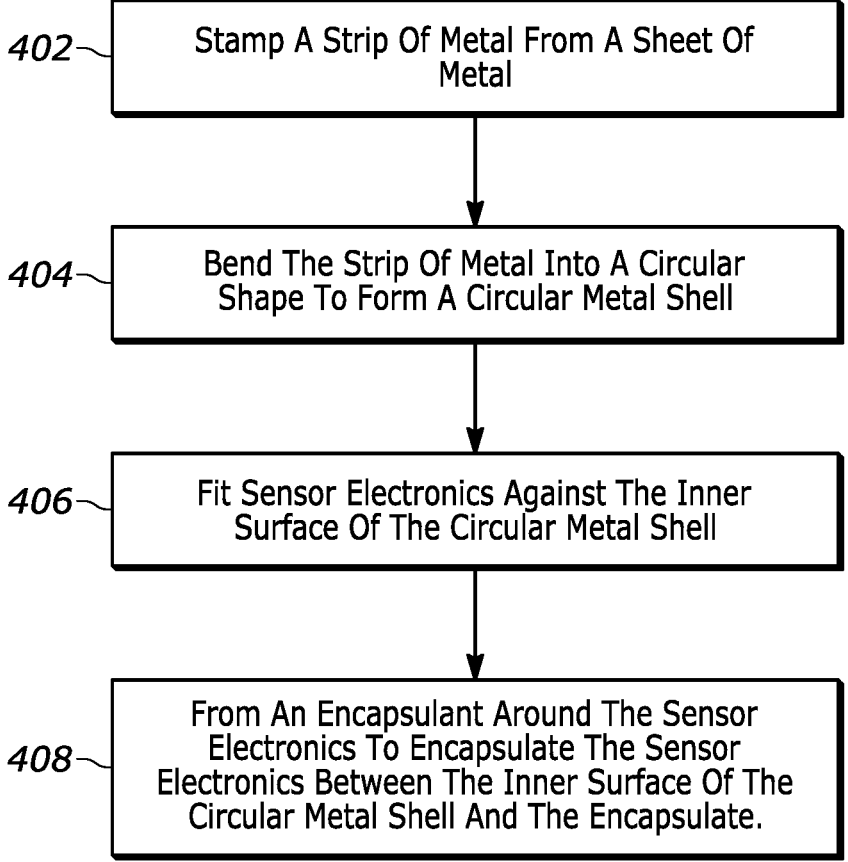

402 — Stamp A Strip Of Metal From A Sheet Of Metal

404 — Bend The Strip Of Metal Into A Circular Shape To Form A Circular Metal Shell 406 — Fit Sensor Electronics Against The Inner Surface Of The Circular Metal Shell 408 — From An Encapsulant Around The Sensor Electronics To Encapsulate The Sensor Electronics Between The Inner Surface Of The Circular Metal Shell And The Encapsulate.

FIG. 4

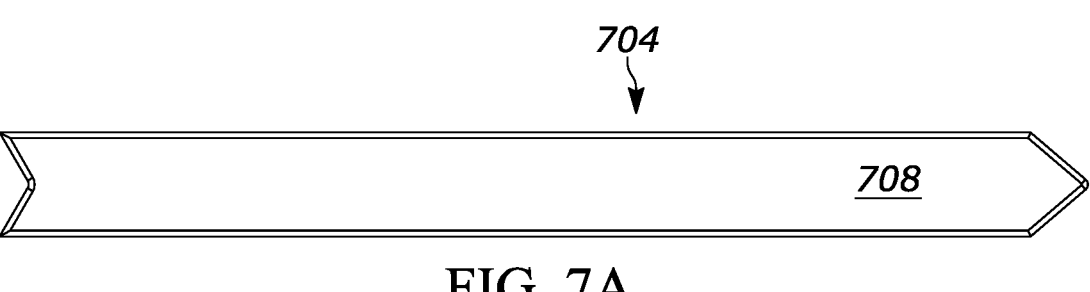
FIG. 7A
FIG. 7B
FIG. 7C
FIG. 7D             FIG. 7E

852

854

800

854

FINGER WEARABLE HEALTH MONITORING DEVICE

CROSS-REFERENCE TO RELATED APPLICATIONS

This application is entitled to the benefit of U.S. Provisional Patent Application Ser. No. 63/358,064, filed on Jul. 1, 2022, which is incorporated by reference herein.

BACKGROUND

Wearable devices that monitor activity and/or health parameters exist in various forms including wrist worn devices and finger worn devices. Whether the device is worn on the wrist or a finger, it is important the device fit correctly for both comfort and performance. Wrist worn devices typically have adjustable wristbands but finger worn devices, such as rings also known as smart rings, have typically been produced in different sizes of rings to fit different sizes of fingers. While producing a range of sizes for smart rings provides options for different sized fingers, the typical smart rings can be difficult to put on and take off and are not able to adapt to changes in finger size due to, for example, temporary swelling.

SUMMARY

A finger wearable health monitoring device is disclosed. In an embodiment, a finger wearable health monitoring device includes a circular metal shell, the circular metal shell comprising a strip of metal that includes an outer surface and an inner surface and two opposing ends, sensor electronics adjacent the inner surface of the circular metal shell, and encapsulant formed over the sensor electronics and on the inner surface of the circular metal shell, and the sensor electronics includes a flexible portion of a circuit board that is opposite the two opposing ends of the circular metal shell.

Other aspects in accordance with the invention will become apparent from the following detailed description, taken in conjunction with the accompanying drawings, illustrated by way of example of the principles of the invention.

BRIEF DESCRIPTION OF THE DRAWINGS

FIGS. 3A-3E are top, side, and end views of a strip of metal after the strip of metal has been stamped from a flat metal sheet but before the strip of metal has been bent into a circular shape.

FIG. 4 is a process flow diagram of a technique for producing a wearable device.

FIGS. 7A-7E are top, side, and end views of a strip of metal in which the edge surface is beveled.

Throughout the description, similar reference numbers may be used to identify similar elements.

DETAILED DESCRIPTION

Figure 1A:
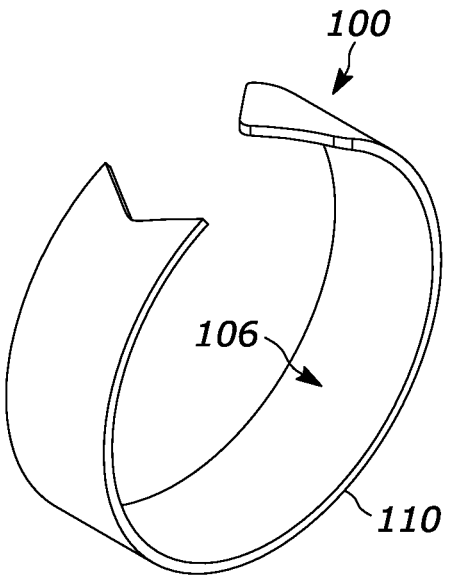
FIGS. 1A and 1B are perspective views of a circular metal shell of a wearable device.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

A finger wearable device, or ring, or smart ring, includes a circular metal shell, sensor electronics, and an encapsulate. In an embodiment, the circular metal shell is formed from a piece of metal, such as a strip of metal, and does not form a complete monolithic circle or ring. Rather, the circular metal shell includes opposing ends that enable the finger wearable device to be designed with some flexibility, e.g., such that the opposing ends of the wearable device are able to move or "flex" relative to each other in response to typical forces encountered from putting the wearable device on a finger, taking the wearable device off of a finger, and/or in response to changes in the size of a finger (e.g., due to swelling). The flexibility of the finger wearable device can enable a user to wear a tighter fitting device in a typical position below a knuckle than would be possible with a finger ring that has no ability to flex. It has been found that a tighter fitting finger wearable device provides more consistent skin to device contact, which can result in better signal generation for an embedded sensor such as an optical and/or radio frequency (RF) sensor.

Circular Metal Shell

Figure 1B:
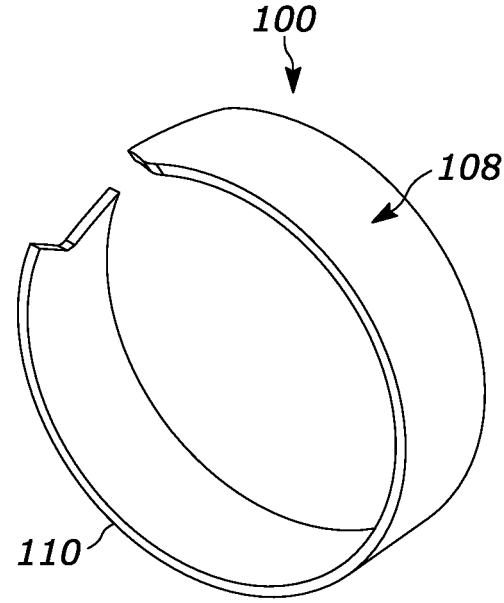
Figure 2A:
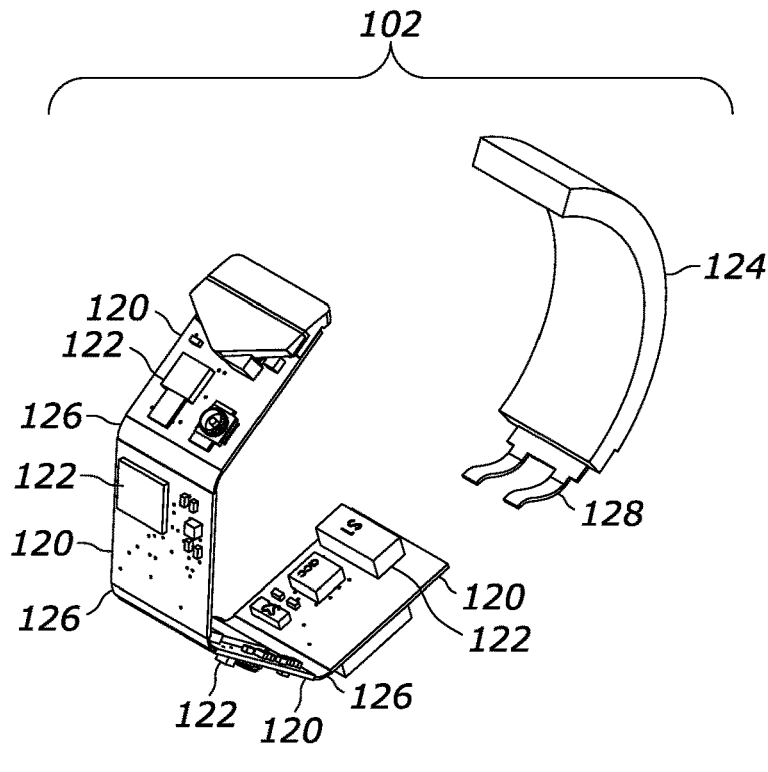
FIGS. 2A and 2B are perspective views of sensor electronics that correspond to the perspective views of the circular metal shell of FIGS. 1A and 1B.
Figure 2B:
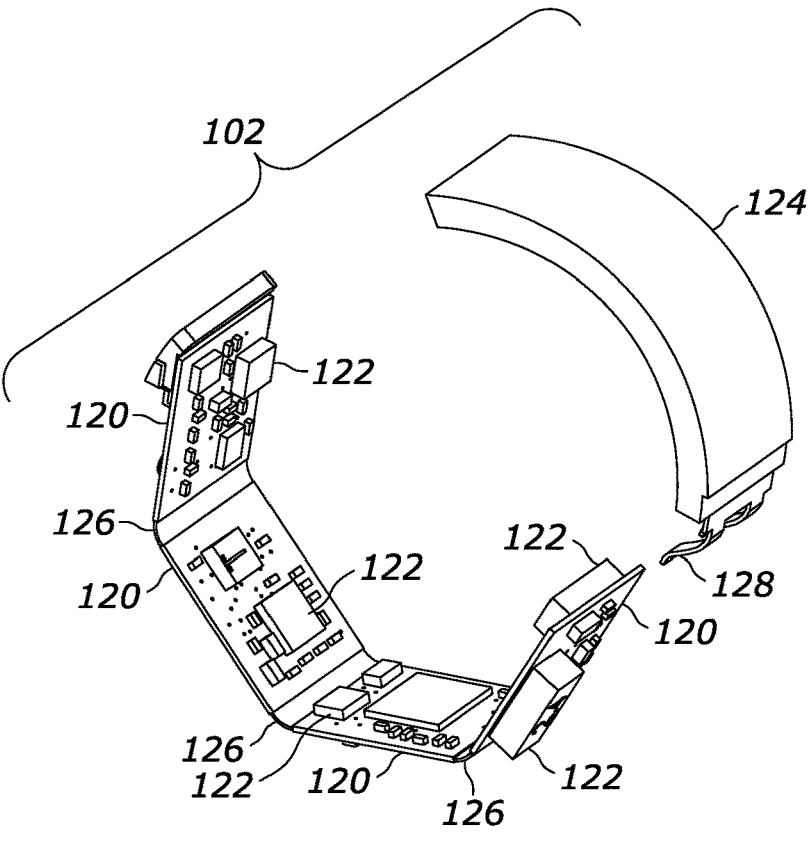

FIGS. 1A and 1B are perspective views of an example of a circular metal shell 100 of a wearable device and FIGS. 2A and 2B are perspective views of sensor electronics 102 that correspond to the perspective views of the circular metal shell.

In an embodiment, the circular metal shell 100 is formed from a strip of metal that includes an inner surface 106, an outer surface 108, and an edge surface 110. Since the wearable device is meant to be worn on a finger, the wearable device has dimensions that accommodate human fingers. In an embodiment, the finger wearable device can be produced in sizes that correspond to standard ring sizes of 4-14, which translates to diameters in the range of approximately 20-29 millimeters. The diameter of a circle that aligns with the circular metal shell can be in the range of, for example, 20-29 millimeters, the width dimension of the circular metal shell may be in the range of, for example, 4.5-10 millimeters, and the width dimension of the edge surface may be in the range of, for example, 0.1-0.7 mm, and preferably in the range of 0.3-0.5 mm, which may also be referred to as the "thickness" of the strip of metal. In such embodiments, the inner surface 106 and the outer surface 108 have width dimensions that are 5-50 times greater than the width dimension of the edge surface 110.

In an embodiment, the circular metal shell 100 is made of a metal such as steel, stainless steel, titanium, or aluminum, although other metals are possible. In an embodiment, the steel is formed to be somewhat flexible at the corresponding dimensions in order to provide some flexibility in response to typical forces encountered from putting the wearable device on a finger, taking the wearable device off of a finger, and/or in response to changes in the size of a finger (e.g., due to swelling). In an embodiment, the circular metal shell is made of spring steel that has a modulus of elasticity that provides a desired level of flexibility.

In an embodiment, the circular metal shell 100 can be formed by bending a flat strip of metal into a circular form. Strips of metal can be formed by stamping a flat sheet of metal to produce individual flat strips of metal having the corresponding dimensions (e.g., length and width dimensions). FIGS. 3A-3F are top, side, and end views of a strip of metal 104 after the strip of metal has been stamped from a flat metal sheet but before the strip of metal has been bent into a circular shape. In an embodiment, the strip of metal has a length dimension in the range of 62-91 mm, a width dimension in the range of 4.5-10 mm, and a thickness (edge dimension) in the range of 0.3-0.5 mm. FIG. 3A shows the outer surface 108 of the strip of metal 104 from a top view, FIG. 3B shows the edge surface 110 of the strip of metal 104 from a first side view, FIG. 3C shows the edge surface 110 of the strip of metal 104 from a second side view (which is opposite the first side view), FIG. 3D shows the edge surface 110 of the strip of metal 104 from a first end view, and FIG. 3E shows the edge surface 110 of the strip of metal 104 from a second end view (which is opposite the first end view). As shown in FIGS. 3A-3E, the strip of metal has a first end 112 (left side) and a second end 114 (right side) that is opposite the first end. Once formed, an individual strip of metal can be bent from a flat strip of metal into a circular shape to form the circular metal shell (FIGS. 1A and 1B, 100). In other embodiments, the circular metal shell may have a different shape, such as a "U" shape in which a trough of the "U" is faced towards the finger when worn, and in which the sensor electronic sit inside the trough formed by the "U" shape of the circular metal shell.

Referring back to FIGS. 1A and 1B, there is a gap, space, or opening between the two ends of the circular metal shell 100, e.g., the two ends of the circular metal shell do not touch each other. As shown in FIGS. 1A and 1B, the two ends of the circular metal shell are opposite each other but are separated by the gap, space, or opening. Thus, although the circular metal shell is circular in shape, the circular metal shell does not form a monolithic circle of metal with no ends and no seams, e.g., as when a metal ring is formed by machining a solid block of metal into a ring. As is described below, because the circular metal shell is not a monolithic circle of metal with no ends and no seams, the finger wearable device is able to have some flexibility. That is, the two ends of the circular metal shell are able to move relative to each other. In an embodiment, the gap between the two ends of the metal is in the range of, for example, 0.1-10 mm in an at rest state, although other gap sizes are possible. Additionally, although in the examples of FIGS. 1A and 1B, the two ends of the circular metal shell are not touching each other, in other embodiments, the two ends of the circular metal shell may be touching each other. However, even if the two ends of the circular metal shell are touching each other, the circular metal shell is not a monolithic circle of metal with no ends and no seams.

The strip of metal 104 (see FIG. 3A) may also include functional features such as through holes and/or cut out sections that are included to provide specific functionality. Additionally, the strip of metal may include decorative features. In an embodiment, the first and/or second ends of the strip of metal may have decorative features such as an arrow shape. The strip of metal may also include decorative features such as coloring, engraving, and/or patterning to provide decorative appeal.

Sensor Electronics

With reference to FIGS. 2A and 2B, the sensor electronics 102 may include various components such as, for example, a circuit board, or circuit boards 120, electronic devices 122, and a battery 124. In an embodiment, the electronic devices are typically mounted on the circuit board and may include IC devices (e.g., packaged IC devices such as a microcontroller, a wireless communications device (e.g., Bluetooth Low Energy), a light emitting devices (LED), sensor devices (optical sensor, RF sensor, temperature sensor, motion sensor (e.g., gyroscope), location sensor (e.g., GPS)) and/or discrete components (e.g., resistors, capacitors, and/or inductors). In an embodiment, the sensor electronics are configured to monitor activity and/or health parameters of the person wearing the device. For example, the sensor electronics can track activity parameters such as motion and location and health parameters such as heart rate, respiration rate, temperature, peripheral oxygen saturation ($SpO_2$), blood pressure, and/or blood glucose level. Although some examples of sensor parameters are described, other parameters may be monitored. Additionally, the sensor electronics may include electronics configured to implement other functionality such as, for example, electronic payments.

The circuit board, or circuit boards 120, may include for example multiple rigid and flat circuit boards connected by flexible portions 126, curved circuit boards, flexible circuit boards, or some combination thereof. In the example embodiment of FIGS. 2A and 2B, the sensor electronics 102 includes four flat circuit boards 120 that are connected to each other by flexible connectors 126 or joints and to which various electronic devices 122 are attached. The sensor electronics also includes the battery 124 electrically connected to the circuit boards and corresponding electronic devices. In the embodiment of FIGS. 2A and 2B, the battery is curved to match the curvature of the circular metal shell 100 (see FIGS. 1A and 1B) and the battery includes electrical connectors 128 that are connectable to the circuit boards to provide power to the various electronic devices.

Assembly Process

FIG. 4 is a process flow diagram of a technique for producing a wearable device. The process involves: 1) at step 402, stamping a strip of metal (e.g., as shown in FIGS. 3A-3E) from a sheet of metal; 2) at step 404, bending the strip of metal into a circular shape to form a circular metal shell; 3) at step 406, fitting the sensor electronics against the inner surface of the circular metal shell; and 4) at step 408, forming an encapsulant around the sensor electronics to encapsulate the sensor electronics between the inner surface of the circular metal shell and the encapsulate. Although an example of a production process is provided, other processes for producing the wearable device are possible. For example, the strips of metal may be formed by a technique other than stamping, such as cutting, molding, or machining, e.g., computer numerical control (CNC) machining. A benefit of the design described herein is that it is possible to form the circular metal shell by bending a flat piece of metal, which enables an efficient manufacturing process when compared to machining individual circular metal parts from a solid block of metal, although the circular metal shell may be formed by a piece of metal that does not start out as flat strip of metal. Additionally, because the circular metal shell is not a monolithic circle of metal, the finger wearable device can be designed to exhibit some flexibility. Other processes for producing the finger wearable device are possible. For example, in another embodiment, the sensor electronics are encapsulated (in an encapsulant) before being fitted against, and attached to, the inner surface of the circular metal shell. The encapsulated sensor electronics are then fit against the inner surface of the circular metal shell.

Figure 5A:
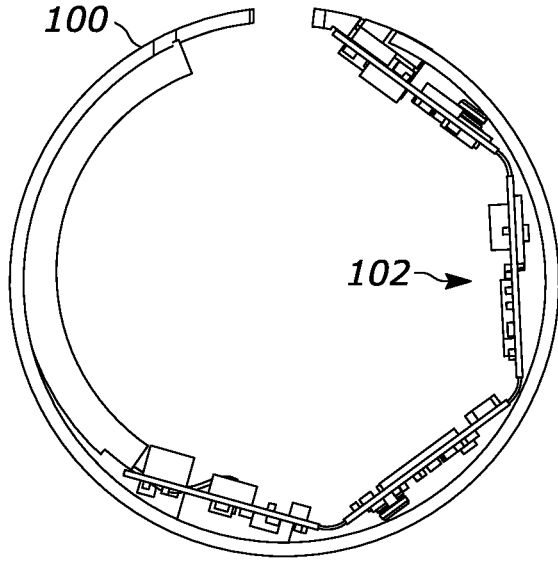
FIGS. 5A-5F are different views of sensor electronics fitted against the inner surface of a circular metal shell.
Figure 5B:
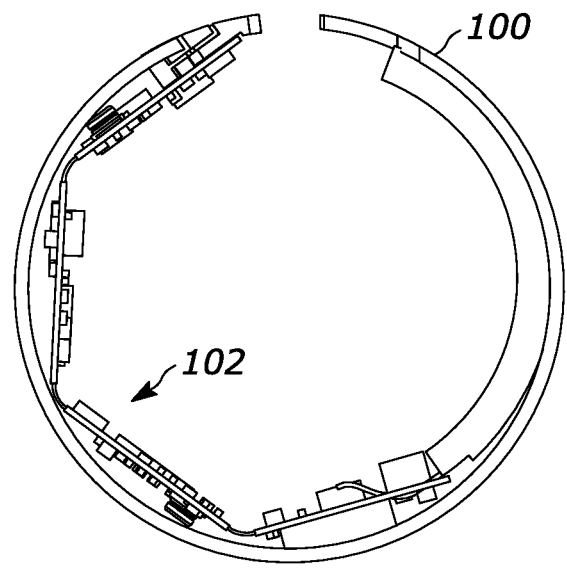
Figure 5C:
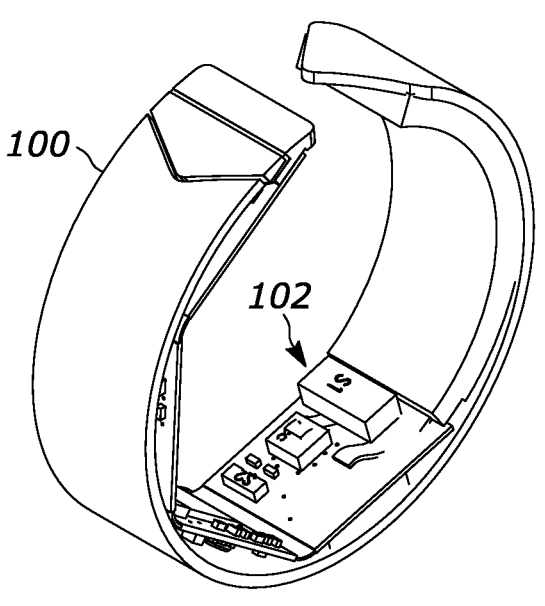
Figure 5D:
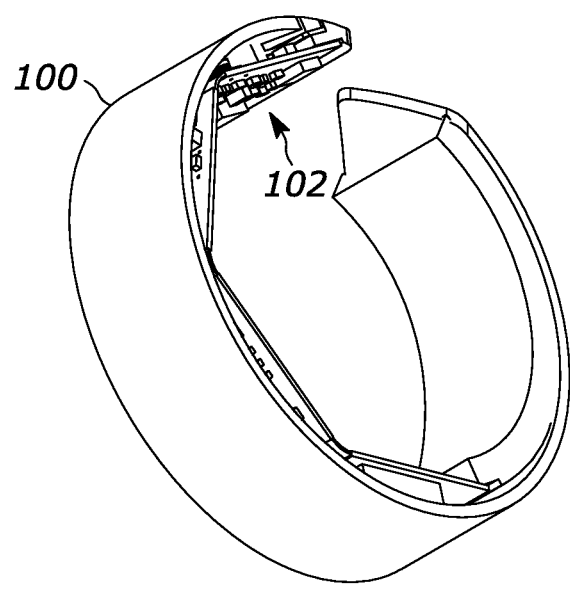
Figure 5E:
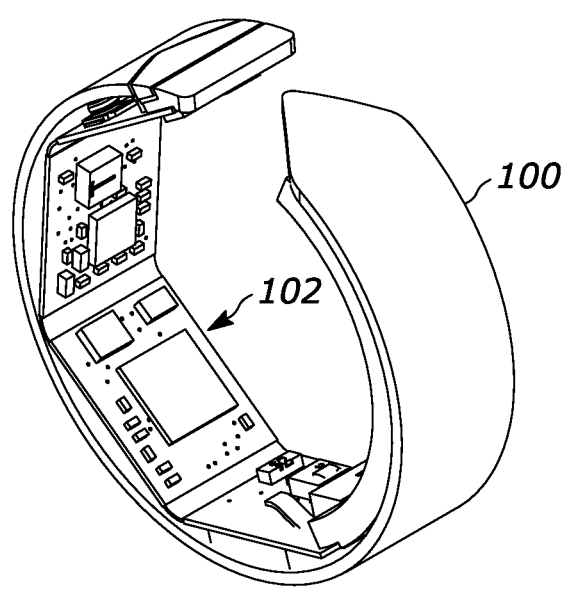
Figure 5F:
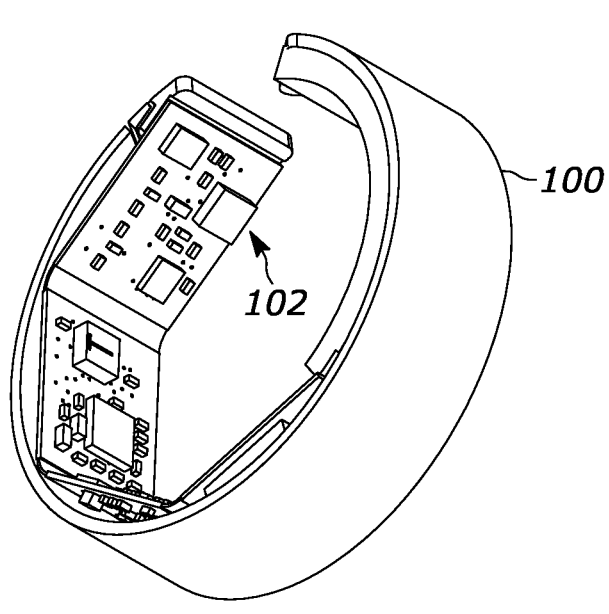

FIGS. 5A-5F are different views of the sensor electronics 102 fitted against the inner surface of the circular metal shell 100. FIG. 5A is a first side view of the circular metal shell and the sensor electronics fitted against the inner surface of the circular metal shell and FIG. 5B is a second side view, which is the opposite side of FIG. 5A, of the circular metal shell and the sensor electronics fitted against the inner surface of the circular metal shell. As shown in FIGS. 5A and 5B, the sensor electronics contact the inner surface of the circular metal shell at various points. The particular points at which the sensor electronics and the inner surface of the circular metal shell contact each other is implementation specific. FIG. 5C is a first perspective view of the circular metal shell and sensor electronics fitted against the inner surface of the circular metal shell, FIG. 5D is a second perspective view of the circular metal shell and sensor electronics fitted against the inner surface of the circular metal shell, FIG. 5E is a third perspective view of the circular metal shell and sensor electronics fitted against the inner surface of the circular metal shell, and FIG. 5F is a fourth perspective view of the circular metal shell and sensor electronics fitted against the inner surface of the circular metal shell. In each perspective view, at least some portion of the inner surface of the circular metal shell, the outer surface of the circular metal shell, and the sensor electronics are visible. In an embodiment, the sensor electronics may be attached to (e.g., glued to) the inner surface of the circular metal shell, at for example, the contact points between the sensor electronics and the circular metal shell.

Encapsulant

Figure 6A:
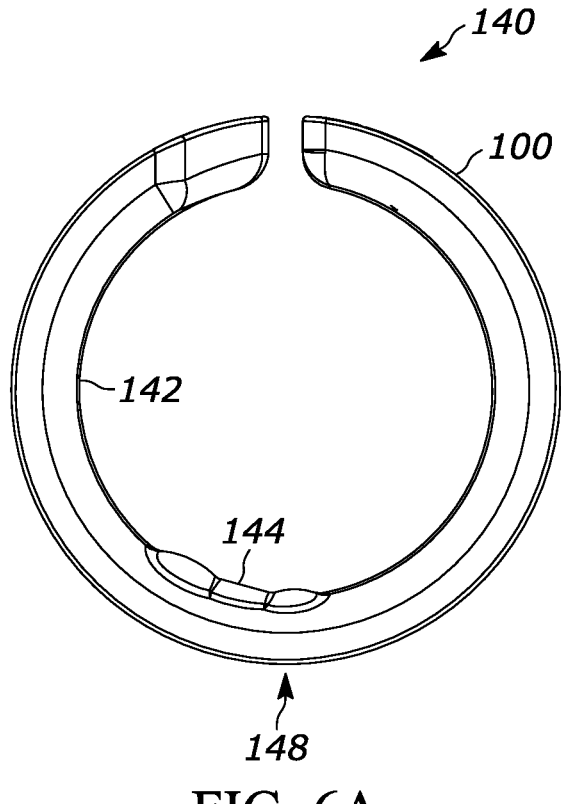
FIGS. 6A-6F are different views of a wearable device that is fully assembled with a circular metal shell, sensor electronics, and an encapsulate.
Figure 6B:
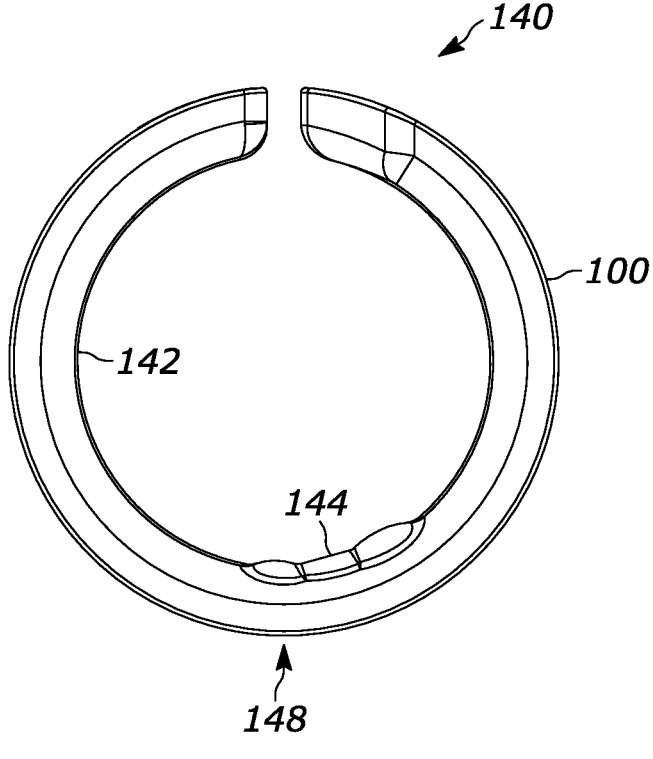
Figure 6C:
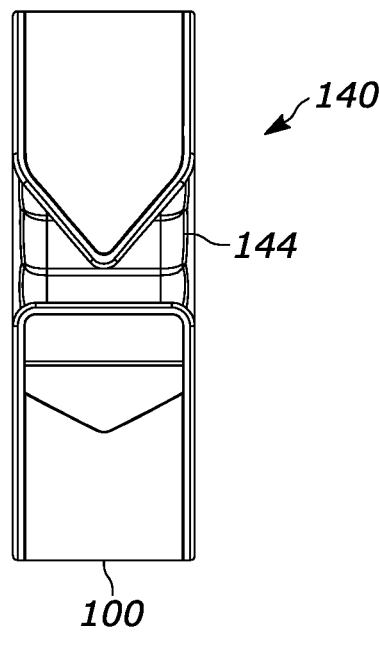
Figure 6D:
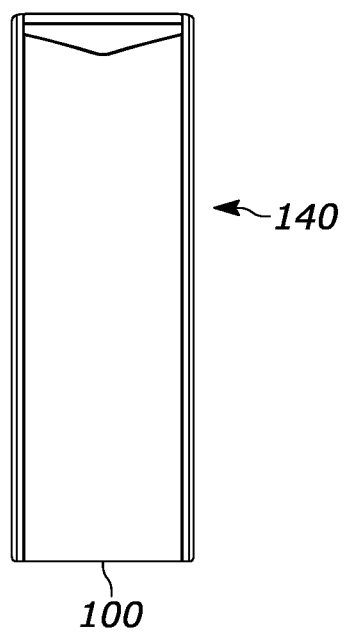
Figure 6E:
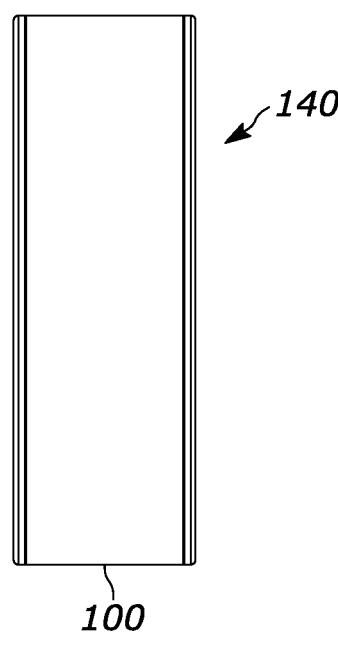
Figure 6F:
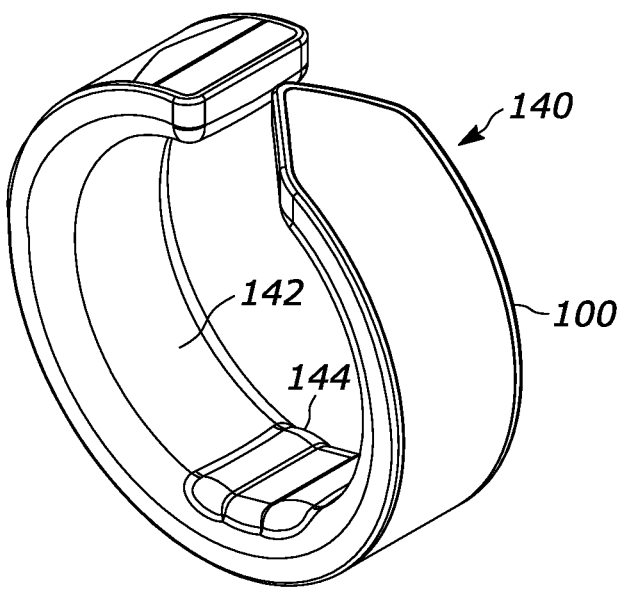

Once the sensor electronics 102 are fitted against the inner surface of the circular metal shell 100 as shown in FIGS. 5A-5F, an encapsulate is formed around the sensor electronics and against the circular metal shell to encapsulate the sensor electronics between the encapsulate and the circular metal shell, e.g., between the encapsulant and the inner surface of the circular metal shell. FIGS. 6A-6F are different views of a finger wearable health monitoring device 140 that is fully assembled with the circular metal shell 100, the sensor electronics (not shown), and the encapsulate (142). In the views of FIGS. 6A-6F, the sensor electronics are not visible through the encapsulate although the sensor electronics are encapsulated between the encapsulate and the circular metal shell. FIG. 6A is a first side view of the finger wearable health monitoring device and FIG. 6B is a second side view of the finger wearable health monitoring device, which is opposite the first side view. In FIGS. 6A and 6B, the circular metal shell 100 and the encapsulant 142 are clearly visible. FIGS. 6C-6E are views of the outer surface of the circular metal shell of the finger wearable health monitoring device, and FIG. 6F is a perspective view of the finger wearable device. In FIGS. 6C-6E, encapsulant can be seen at the edges of the finger wearable health monitoring device and in FIG. 6C, encapsulant can be seen through the gap between the first and second ends of the circular metal shell. As is shown in FIGS. 6A, 6B, and 6F, the encapsulant is formed to have a smooth inner surface that promotes comfort for the person wearing the device. The encapsulant may include one or more raised portions 144, e.g., portions or "bubbles" of the encapsulant that are raised above the inner smooth surface of the encapsulant. Such raised portions of the encapsulant may be formed to encapsulate larger components of the sensor electronics, to serve as a lens for light from an optical sensor, and/or to provide better contact between the encapsulant and the skin of the person wearing the device. In an embodiment, the raised portion is aligned with the location of a sensor such as an optical sensor so that the raised portion is directly below the sensor. In an embodiment, as is visible in FIGS. 6A, 6B, 6C (partially), and 6F, the raised portion 144 of the encapsulate 142 spans the width of the circular metal shell 100 and the sensor electronics and is aligned with a sensor, such as an optical sensor, of the sensor electronics. Having a raised portion of the encapsulant that corresponds to the location of an optical sensor and extends across the width of the circular metal shell has been found to promote more consistent contact with the skin and result in improved signal quality from the optical sensor. In an embodiment, the raised portion is formed by a mold that forms the entire shape of the encapsulant in a single injection molding process. In another embodiment, the raised portion, or portions, are formed separately from the encapsulant, for example, with a separate piece of plastic that is attached (e.g., glued) to the encapsulant to form a raised, "pillow" or "bubble," portion after the encapsulant has been cured. In an embodiment, an opaque and/or reflective material may be added to the edges of the raised portion to prevent light from a corresponding optical sensor from "leaking" out the sides of the raised portion. For example, some paint (e.g., white paint) may be applied on the edges of the raised portion so that light emitted from the optical sensor is directed through that raised portion at the interface between the skin and the raised portion, which can result in improved signal quality from the optical sensor.

The encapsulant may be transparent, partially transparent, or opaque. The encapsulant may be clear or colored.

Flexibility of the Circular Metal Shell and the Encapsulant

As shown in FIGS. 6A-6C and 6F, the finger wearable device 140 is not a monolithic circle of metal and encapsulant. Because the finger wearable device is not a monolithic circle of metal and encapsulant, the finger wearable device is able to have some flexibility, e.g., such that opposing ends of the finger wearable device are able to move or "flex" relative to each other in response to typical forces encountered from putting the wearable device on a finger, taking the wearable device off of a finger, and/or in response to changes in the size of a finger (e.g., due to swelling). The flexibility of the finger wearable device enables a user to wear a tighter fitting device in a typical position below a knuckle than may be possible with a wearable finger ring that has no ability to flex. It has been found that a tighter fitting finger wearable device provides more consistent skin to device contact, which can result in better signal generation from a sensor such as an optical and/or radio frequency (RF) sensor. In some embodiments, the flexibility of the circular metal shell and the flexibility of the encapsulant are matched to each other.

Figure 6G:
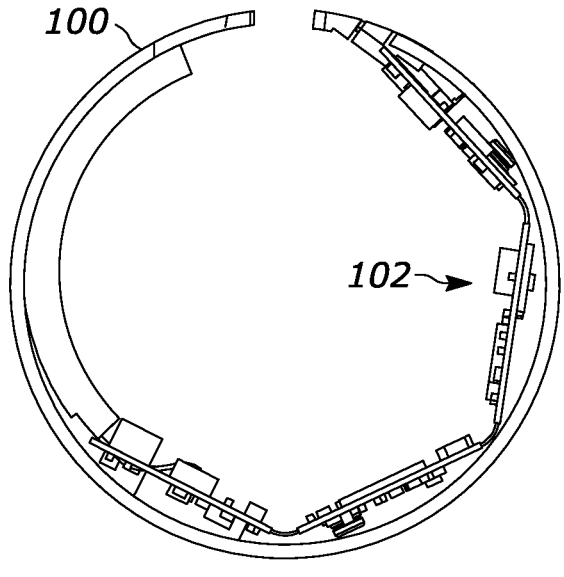
FIGS. 6G and 6H are different views of sensor electronics fitted against the inner surface of a circular metal shell in which a flexible portion of the circuit board that connects two rigid portions of the circuit board is opposite the opening in the ring.
Figure 6H:
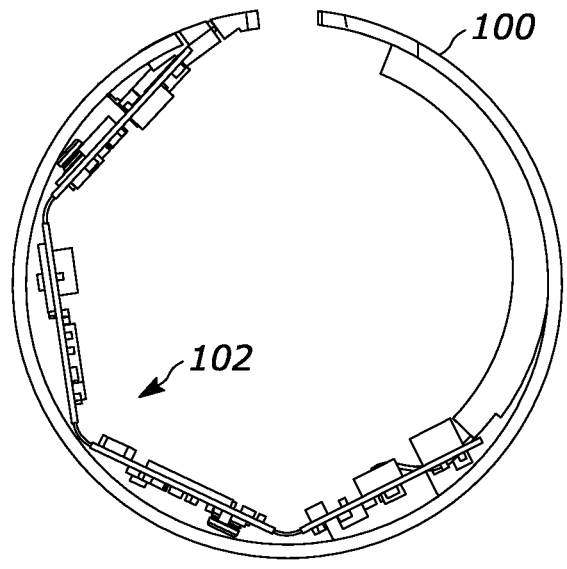
Figure 8A:
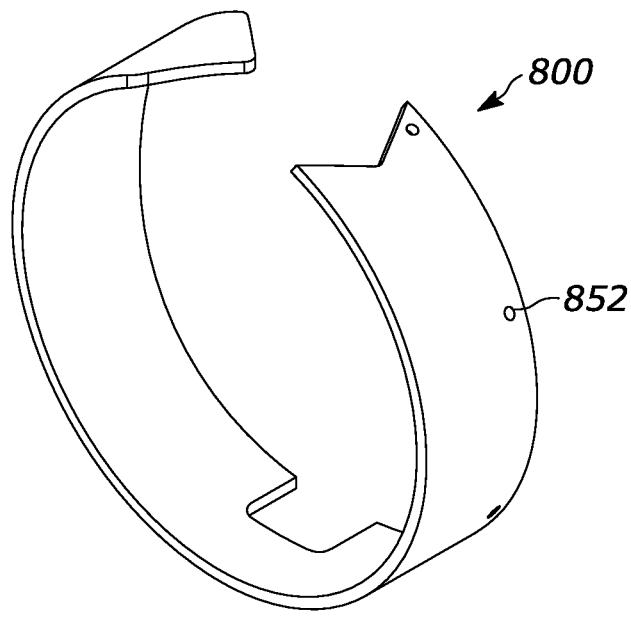
FIGS. 8A-8J are views of a circular metal shell in which the circular metal shell includes various features such as through holes and cut out portions.
Figure 8B:
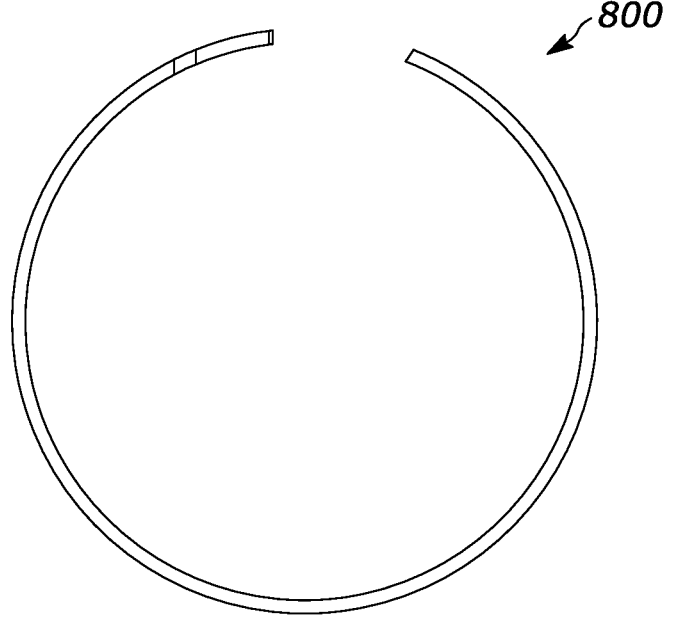
Figure 8C:
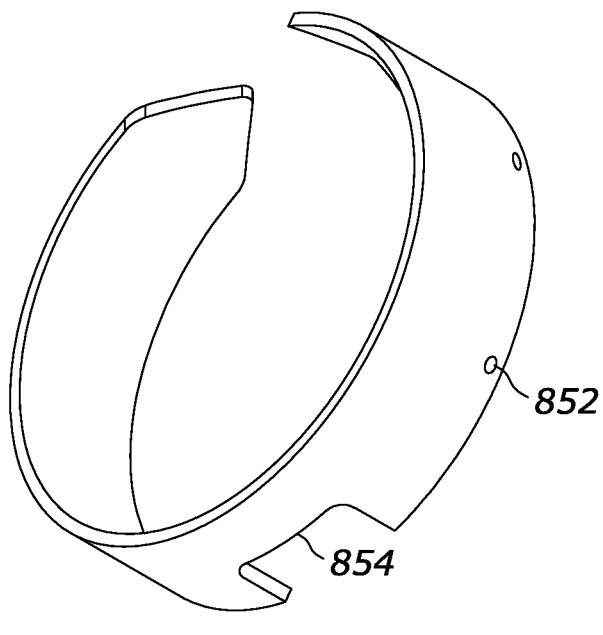
Figure 8D:
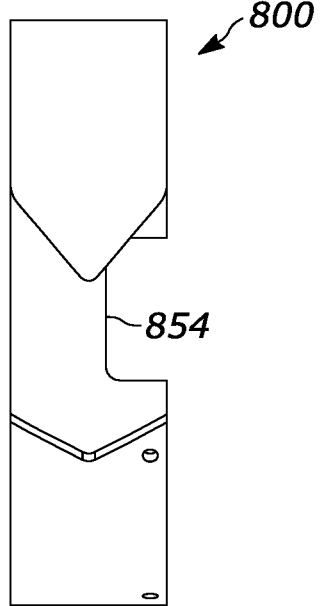
Figure 8E:
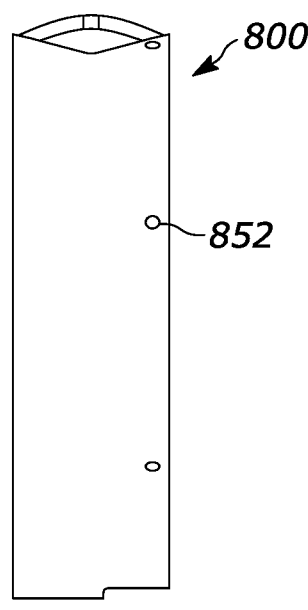
Figure 8F:
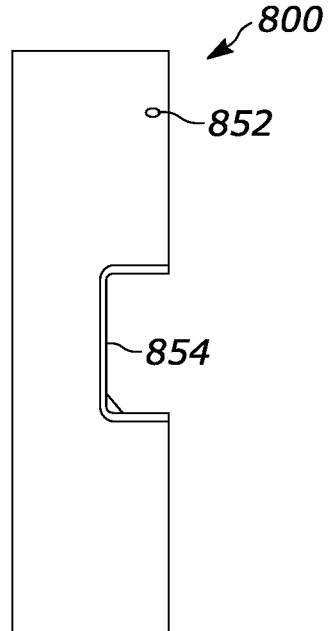
Figure 8G:
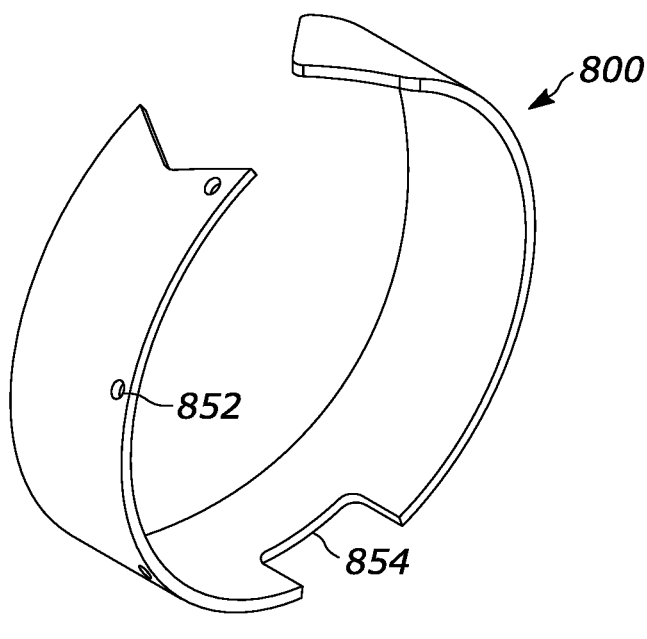
Figure 8H:
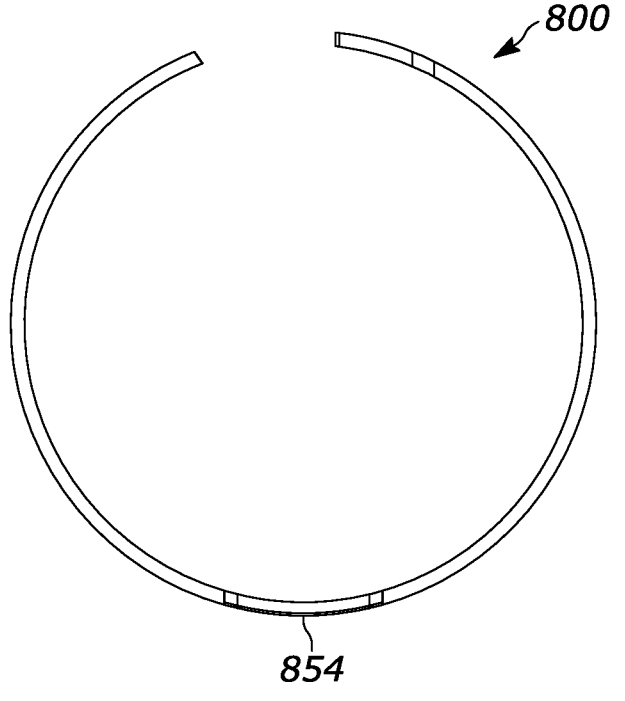
Figure 8I:
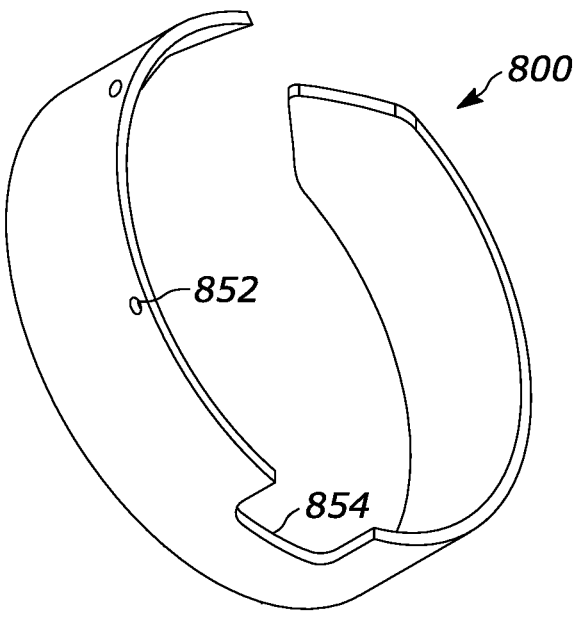
Figure 8J:
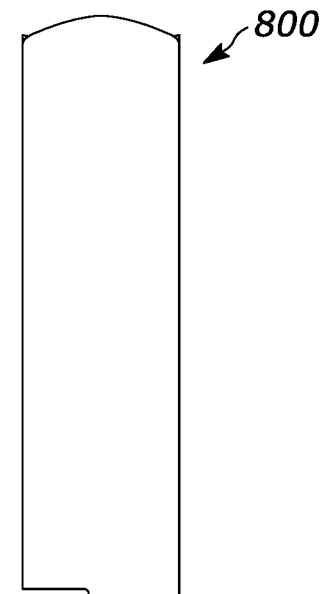

Additionally, it has been found that the finger wearable device will tend to experience the greatest flexing at a point that is opposite the opening. That is, when a spreading force is applied to the ring, e.g., from putting the ring on a finger, taking the ring off a finger, from finger swelling, or from some other externally applied force, the greatest stress and/or strain experienced by the finger wearable device is experienced at the portion of the wearable device that is opposite the opening that is formed by the two opposing ends (e.g., opposite along a line that passes through the opening between the two opposing ends and through the center point of a circle that is defined by the wearable device). For example, with reference to FIGS. 6A and 6B, the greatest stress and/or strain may be experienced by the finger wearable device 140 at or near the location indicated by the arrows 148. Given that the finger wearable device will tend to experience the greatest stress and/or strain at a known location, in some embodiments, the sensor electronics are configured so that a more flexible portion of the sensor electronics is aligned with such a location. For example, a flexible portion of the circuit board is positioned at such a location. For example, the sensor electronics are specifically designed and placed within the circular metal shell such that a flexible portion that connects two pieces of circuit board is aligned with the location of greatest stress/strain (e.g., a position that is opposite of the two opposing ends of the circular metal shell. FIGS. 6G and 6H show different views of the sensor electronics fitted against the inner surface of the circular metal shell 100 in which a flexible portion of the circuit board 126 that connects two rigid portions 120 of the circuit board is opposite the opening in the ring (e.g., opposite along a line that passes through the opening and through the center point of a circle that is defined by the ring).

Features of the Circular Metal Shell

In some embodiments, the circular metal shell may include a feature or features that promote adherence between the encapsulate and the circular metal shell. For example, the inner surface of the circular metal shell may include a rough texture that promotes adhesion of the encapsulate to the inner surface of the circular metal shell. In an embodiment, the texture may be a feature of a sheet of metal before the strips are stamped from the sheet of metal. In another embodiment, the circular metal shell may include features such as through holes that promote adhesion between the metal and the encapsulant.

In another embodiment, the edge surface of the strip of metal may be beveled to promote adhesion between the metal and the encapsulant. FIGS. 7A-7E are top, side, and end views of a strip of metal (before being bent into a circular metal shell) in which the edge surface is beveled. FIG. 7A shows the outer surface 708 of the strip of metal 704 from a top view, FIG. 7B shows the edge surface 710 of the strip of metal from a first side view, FIG. 7C shows the edge surface 710 of the strip of metal from a second side view (which is opposite the first side view), FIG. 7D shows the edge surface 710 of the strip of metal from a first end view, and FIG. 7E shows the edge surface 710 of the strip of metal from a second end view (which is opposite the first end view). In the example of FIGS. 7A-7E, the width dimension of the inner surface (not shown) of the metal strip is slightly larger than the width dimension of the outer surface 708 of the metal strip such that a plane of the edge surface 710 is not orthogonal to a plane of the inner surface of the metal strip or to a plane of the outer surface of the metal strip. For example, the width dimension of the inner surface of the metal strip may be 0.1-2 mm larger than the width dimension of the outer surface of the metal strip. In an embodiment, the beveling provides an angled surface around which encapsulant can be formed to provide tight coupling between the circular metal shell and the sensor electronics. Other edge features, such as a ridge or groove may be provided to promote tight coupling between the metal and the encapsulant.

Miscellaneous Options

FIGS. 8A-8J are views of the circular metal shell 800 in which the circular metal shell includes various features such as through holes 852 and cut out portions 854. For example, the circular metal shell may include one or more through holes that extend from the inner surface of the metal strip to the outer surface of the metal strip. Such through holes can be filled with encapsulate to provide adherence between the encapsulate and the circular metal shell. For example, the cutout portion may provide clearance for a wireless interface such as low energy wireless interface. In an embodiment, the features may be used for aligning the sensor electronics relative to the circular metal shell while fitting the sensor electronics against the inner surface of the circular metal shell.

Figure 9:
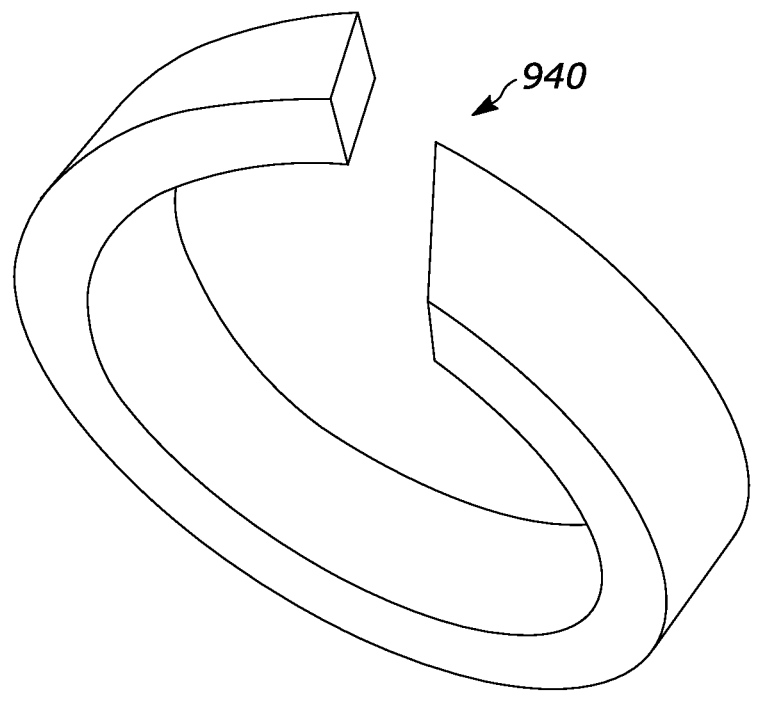
FIG. 9 is an example of a wearable device that has a spiral shape.

In the embodiments described with reference to FIGS. 1A, 1B, 5A— and 6A-6F, the circular metal strip has a "planar" configuration in which a center of a circle that corresponds to the circular metal shell and a center line of the strip of metal are coplanar. That is, a plane could be fit to intersect the centerline of the metal strip and the center of a circle that is at least partially formed by the circular metal shell or the finger wearable device could lay flat against a flat surface with an entire side edge of the wearable device in contact with the flat surface when the device is resting on the flat surface. However, in other embodiments, the circular metal shell and the corresponding wearable device may have a "spiral" shape. FIG. 9 is an example of a finger wearable device 940 that includes the same components as the finger wearable devices described with reference to FIGS. 1A, 1B, 5A-5F, and 6A-6F except that the finger wearable device has a spiral shape. With a spiral shape, the entire side of the wearable device is not in contact with a flat surface when the finger wearable device is at rest on its side on the flat surface. In an embodiment, the circular metal shell is formed by bending a flat strip of metal into a spiral shape. Other configurations of the finger wearable device are also possible. For example, the finger wearable device may have a "twisted" shape in which a strip of metal is bent into a circular shape and also rotated or twisted at least 180 degrees such that portions of the opposite sides of the metal strip form both the inner surface of the circular metal shell and the outer surface of the circular metal shell.

In an embodiment, a circular metal shell has the general shape of at least a portion of a circle. For example, the circular shape of the element (e.g., the circular metal shell, sensor electronics, and/or encapsulant) has an identifiable center and radius.

Figure 10:
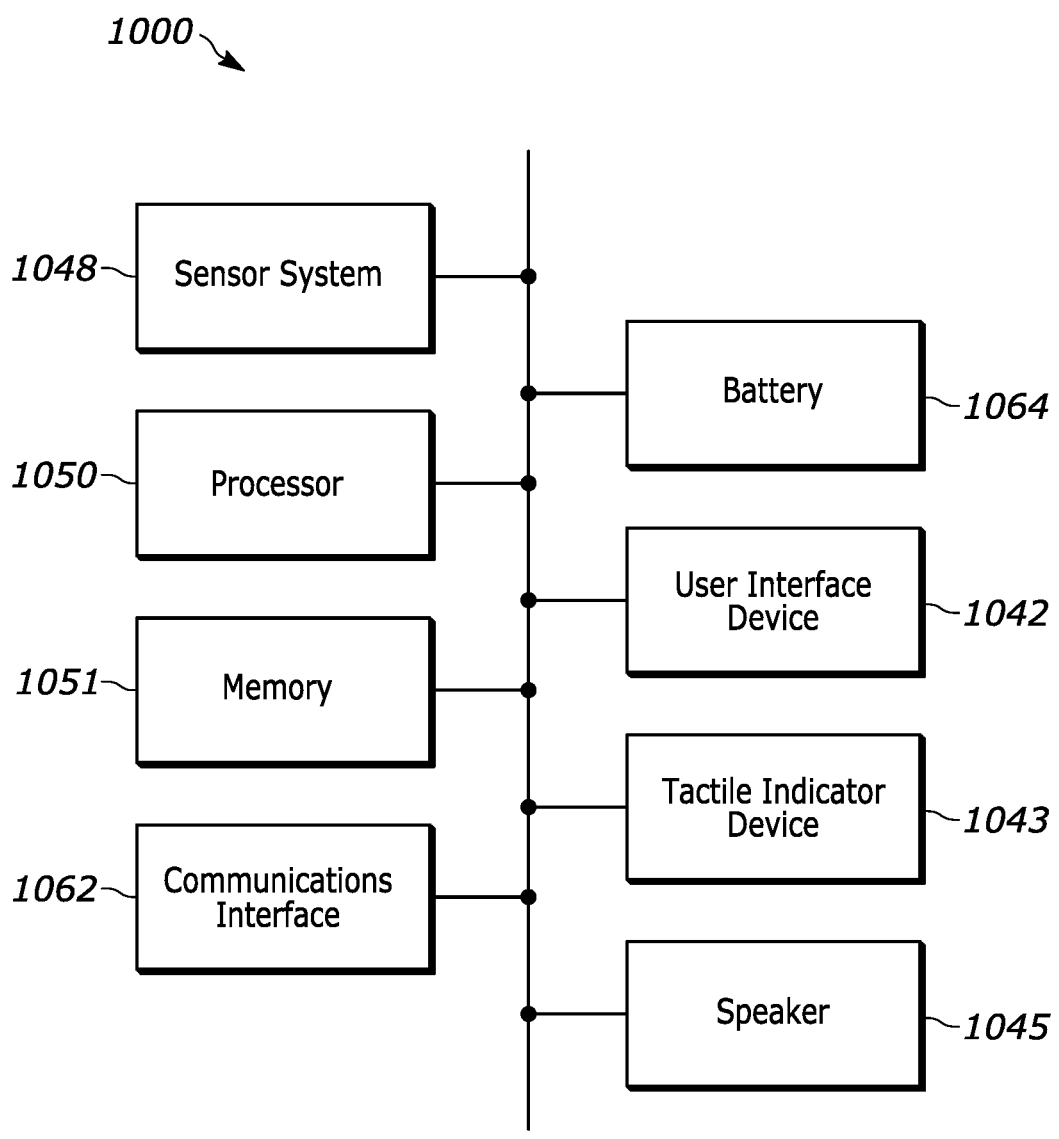
FIG. 10 is an example computing system that includes a sensor system, a processor, memory, a communications interface, a battery, a user interface device, a tactile indicator device, and a speaker.

FIG. 10 is an example computing system 1000 that includes a sensor system 1048, a processor 1050, memory 1051, a communications interface 1062, a battery 1064, a user interface device 1042, a tactile indicator device 1043, and a speaker 1045. The computing device may be embodied as a finger wearable device, including, for example, a finger ring as disclosed herein. The computing device may include all of the components or some portion of the components. In an embodiment, the tactile indicator device may include a mechanism that generates tactile feedback (e.g., a vibration) in response to electrical control signal. The sensor system may comprise an optical sensor, an RF-based sensor, and/or some other sensing mechanism. The processor, memory, communications interface, battery, user interface and speaker may be elements as are known in the field.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:
1. A finger wearable health monitoring device comprising:
a circular metal shell, the circular metal shell comprising a piece of metal that includes an outer surface and an inner surface and two opposing ends;
sensor electronics adjacent the inner surface of the circular metal shell; and
encapsulant formed over the sensor electronics and on the inner surface of the circular metal shell;

wherein the sensor electronics includes a flexible portion of a circuit board that is opposite the two opposing ends of the circular metal shell.

2. The finger wearable health monitoring device of claim 1, wherein the circular metal shell and the encapsulant have matching flexibility.

3. The finger wearable health monitoring device of claim 1, wherein the encapsulant includes a raised portion that spans the width of the circular metal shell to promote contact between the raised portion and skin of a finger.

4. The finger wearable health monitoring device of claim 1, wherein the encapsulant includes a raised portion that spans the width of the circular metal shell.

5. The finger wearable health monitoring device of claim 4, wherein the raised portion includes an opaque material on side surfaces of the raised portion.

6. The finger wearable health monitoring device of claim 1, further including a raised portion that is attached to the encapsulant to promote contact between the raised portion and skin of a finger.

7. The finger wearable health monitoring device of claim 1, further including a raised portion that is attached to the encapsulant.

8. The finger wearable health monitoring device of claim 7, wherein the raised portion includes an opaque material on side surfaces of the raised portion.

9. The finger wearable health monitoring device of claim 1, wherein the piece of metal of the circular metal shell is a strip of metal and wherein the circular metal shell is formed by bending the strip of metal into a circular shape.

10. The finger wearable health monitoring device of claim 9, wherein the strip of metal is flat before being bent into the circular shape.

11. The finger wearable health monitoring device of claim 9, wherein the strip of metal includes an edge surface that connects the inner surface to the outer surface.

12. The finger wearable health monitoring device of claim 11, wherein the inner surface and outer surface have width dimensions that are 5-50 times greater than a width dimension of the edge surface.

13. The finger wearable health monitoring device of claim 9, wherein the inner surface has a width dimension that is larger than the outer surface.

14. The finger wearable health monitoring device of claim 9, wherein the inner surface has a width dimension that is larger than the outer surface such that an edge surface is angled at a non-orthogonal angle relative to the inner surface and the outer surface.

15. The finger wearable health monitoring device of claim 14, wherein the encapsulant is formed at least partially around the edge surface.

* * * * *